United States Patent
Yu (10) Patent No.: US 8,031,835 B2
(45) Date of Patent: Oct. 4, 2011

(54) METHOD AND SYSTEM FOR TRANSLATIONAL DIGITAL TOMOSYNTHESIS MAMMOGRAPHY

(75) Inventor: Xinsheng Cedric Yu, Clarksville, MD (US)

(73) Assignee: Xcision Medical Systems LLC, Columbia, MD (US)

( * ) Notice: Subject to any disclaimer, the term of this patent is extended or adjusted under 35 U.S.C. 154(b) by 81 days.

(21) Appl. No.: 12/537,421

(22) Filed: Aug. 7, 2009

(65) Prior Publication Data

US 2010/0034348 A1    Feb. 11, 2010

Related U.S. Application Data (60) Provisional application No. 61/188,236, filed on Aug. 7, 2008.

(51) Int. Cl.
| | |
|---|---|
| *A61B 6/04* | (2006.01) |
| *G01N 23/083* | (2006.01) |
| *G01N 23/04* | (2006.01) |
| *H05G 1/02* | (2006.01) |

(52) U.S. Cl. ............. 378/37; 378/4; 378/22; 378/196
(58) Field of Classification Search .......... 378/37, 378/98.11, 4, 22, 196
See application file for complete search history.

(56) References Cited

U.S. PATENT DOCUMENTS

| | | | | |
|---|---|---|---|---|
| 6,463,122 | B1* | 10/2002 | Moore | 378/65 |
| 6,480,565 | B1* | 11/2002 | Ning | 378/37 |
| 6,987,831 | B2* | 1/2006 | Ning | 378/37 |
| 7,142,633 | B2* | 11/2006 | Eberhard et al. | 378/62 |
| 7,298,816 | B2* | 11/2007 | Moore et al. | 378/37 |
| 7,566,172 | B2* | 7/2009 | Kashiwagi | 378/205 |
| 7,763,864 | B2* | 7/2010 | Formenti | 250/453.11 |
| 2001/0054695 | A1* | 12/2001 | Lienard et al. | 250/368 |
| 2007/0036267 | A1* | 2/2007 | Becker et al. | 378/65 |
| 2007/0064867 | A1* | 3/2007 | Hansen et al. | 378/37 |
| 2007/0282221 | A1* | 12/2007 | Wang et al. | 600/564 |
| 2008/0043905 | A1* | 2/2008 | Hassanpourgol | 378/37 |

* cited by examiner

Primary Examiner — Edward J Glick
Assistant Examiner — Thomas R Artman
(74) Attorney, Agent, or Firm — Carol Larcher; Larcher & Chao Law Group (57) ABSTRACT

A method of imaging a breast comprising (i) having a patient lie prone on a computer-controlled couch, which comprises a channel or left and right openings, and position the left or right breast of the patient in the channel or the left or right opening, respectively, and (ii) repeatedly imaging the breast using a scanning x-ray source while moving the couch down and up, such that the breast moves down and up in the field between the source of radiation and the detector, which method can further comprise constructing a three-dimensional image of the breast in its natural shape and analyzing the three-dimensional image of the breast; and a system for use in such a method.

15 Claims, 7 Drawing Sheets

Trajectory of X-ray Source
forms a zigzag pattern in a curved plane

METHOD AND SYSTEM FOR TRANSLATIONAL DIGITAL TOMOSYNTHESIS MAMMOGRAPHY

CROSS-REFERENCE TO RELATED APPLICATION(S)

This application claims priority to U.S. provisional patent application No. 61/188,236, which was filed on Aug. 7, 2008.

TECHNICAL FIELD

The present disclosure relates to a method and system for using digital tomosynthesis mammography (DTM) translationally in the absence of pressing plates.

BACKGROUND

Over the last few decades, mammography and ultrasound have served as the main screening tools to detect breast cancer. With the increase in availability of magnetic resonance imaging (MRI), comparisons have been made between mammography, alone or in further combination with ultrasound, and MRI in the detection of breast cancer. It has been reported that MRI is twice as sensitive as, and three times more specific than, mammography (Kuhl et al., J. Clin. Oncol. 23: 8469-8476 (2005)). MRI is even more effective than mammography in combination with ultrasound in accurately defining the extent and type of disease (Kuhl et al. (2005), supra; and Berg et al., Radiology 233: 830-849 (2004)). Unfortunately, MRI is much more costly than mammography and ultrasound, even when mammography and ultrasound are used in combination, and the imaging procedures takes much longer. Therefore, the use of MRI is currently limited to patients at high risk for developing breast cancer.

Tomosynthesis (Suryanarayanan et al., Acad. Radiol. 7(12): 1085-1097 (2000)) and breast computed tomography (CT) (Boone et al., Radiology 221: 657-667 (2001)) are three-dimensional (3-D) imaging technologies currently under development. It is expected that at least one of these technologies will eventually replace digital mammography as the tool of choice in the screening and diagnosis of breast cancer. Although these technologies offer advantages over mammography, they also present some major disadvantages. For example, the breast CT, while it rotates a low kilo Volt (kV) x-ray source around the breast of a patient in the prone position and can image the ductal system of the breast and tumors, it cannot image the tissues of the breast close to the chest wall and any tumors that might occur there. Digital tomosynthesis mammography (DTM) involves generating two-dimensional projection-view images, which are reconstructed to provide three-dimensional structural information of the imaged portion of the breast; however, the two-dimensional projection-view images are generated from a limited number of angles over a limited angular range (Zhang et al., Med. Phys. 33(10): 3781-3795 (2006)). Given the limited projections, clear images can only be generated in a limited thickness of breast tissues. While DTM may be suitable for the set-up used for mammography, i.e., pressing the breast into a uniform thickness between two plastic plates, it cannot image the entire breast in its natural shape. It is the aforementioned disadvantages that render these technologies, in their current state, unsuitable for imaging of the breast for treatment of a tumor using surgery, radiation, or another targeted treatment modality. The inability to image tumors close to the chest wall and the inability to image the breast in its natural state make it difficult for a surgeon to rely on such images to determine accurately the location of a tumor for complete surgical removal and/or thorough treatment with radiation or another therapeutic agent. The inability to determine accurately the location of a tumor for surgical removal contributes to repeat lumpectomies, about 30% of which result in excised tissues containing malignant cells on their margins.

In view of the foregoing, it is an object of the present disclosure to provide a method and a system for using DTM translationally in the absence of pressing plates. This and other objects, as well as inventive features, will become apparent from the detailed description provided herein.

SUMMARY

A method of imaging a breast of a human is provided. The method comprises (i) having a patient lie prone on a computer-controlled couch, which comprises a channel or left and right openings, and position the left or right breast of the patient in the channel or the left or right opening, respectively, for imaging; and (ii) repeatedly imaging the breast using a scanning x-ray source while moving the couch down and up, such that the breast moves down and up in the field between the source of radiation and the detector. X-rays of different energy potential can be used in each direction of movement of the breast in the field between the source of radiation and the detector. The method can further comprise constructing a three-dimensional image of the breast in its natural shape, optionally while employing dual energy digital subtraction, alone or in further combination with analyzing the three-dimensional image of the breast, such as for diagnosis or therapy.

Also provided is a system for imaging of the breast. The system comprises (i) a couch comprising a channel or right and left openings for placement of the right and left breasts, respectively, a base support, at least one motor, which is operably connected to the couch and which moves the couch in a vertical axis of motion, and a computerized control system, which controls the movement of the couch, (ii) an x-ray source, and (iii) a detector. The system optionally comprises a layer of a self-molding medium on the top surface of the couch, and/or one or two breast shields, which are removeably attached to the couch or slidably mounted to the channel.

DETAILED DESCRIPTION

Figure 1A:
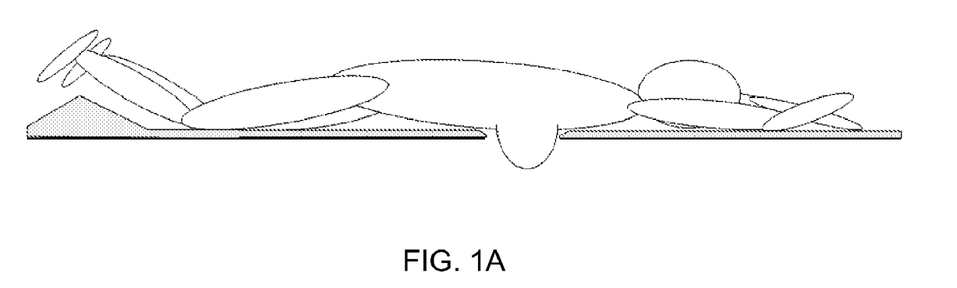
FIG. 1a is a side view of a patient lying prone on a couch with her right breast positioned in a channel (or right opening) in the couch.

A method of imaging a breast of a human is provided. The method comprises (i) having a patient lie prone (see FIG. 1a), which is a side view of a patient lying prone on a couch with her right breast positioned in a channel (or right opening) in the couch, and FIG. 1b, which is a head-on view of a patient lying prone on a couch with her right breast positioned in a channel (or right opening) of the couch relative to the x-ray tube and detector) on a computer-controlled couch, which comprises a channel or left and right openings, and position the left or right breast of the patient in the channel or the left or right opening, respectively, for imaging; and (ii) repeatedly imaging the breast using a scanning x-ray source while moving the couch down and up, such that the breast moves down and up in the field between the source of radiation and the detector. Preferably, imaging is continued until a sufficient number of cross-sectional images have been obtained to construct a three-dimensional image of the breast in its natural shape with uniform resolution. The method enables the entire breast to be imaged without pressing between plates.

While the method is described herein with the breast moving down (relative to the field, i.e., with the breast not yet in the field or only part of the breast, such as the nipple, in the field) and up, it is to be understood that the breast can start in a down position (relative to the field, i.e., with the breast all of the way in the field) and move up. In this regard, the imaging of the breast can start at some point midway between the breast being completely in the field or completely out of the field. Likewise, the scanning x-ray source can start in a down position (relative to the couch, i.e., further from the couch) and move up, start in an up position (relative to the couch, i.e., closer to the couch) and move down, or start somewhere in between and then move in either the up or down direction. Furthermore, the movement of the breast and the movement of the x-ray source do not necessarily have to be in the same direction; for example, they can move towards each other and then away from each other. Desirably, the movement of the breast and the x-ray source is such that scanning time is kept to a minimum. In this regard, the x-ray source can comprise an array of tubes (as described herein below), which are fired in a programmed sequence such that the x-ray source does not have to be moved to scan the breast. When "scanning" is used herein, it is intended to encompass scanning achieved by movement of an x-ray source as well as scanning achieved by firing of x-ray tubes in an array in accordance with a programmed sequence, e.g., consecutively. Desirably, all of the volume elements, referred to as "voxels," of the breast are traversed by the radiation beam many times from different directions, while exposing the breast to only as much radiation as is necessary to obtain enough images of the breast to enable a uniform three-dimensional reconstruction of the breast.

Figure 2A:
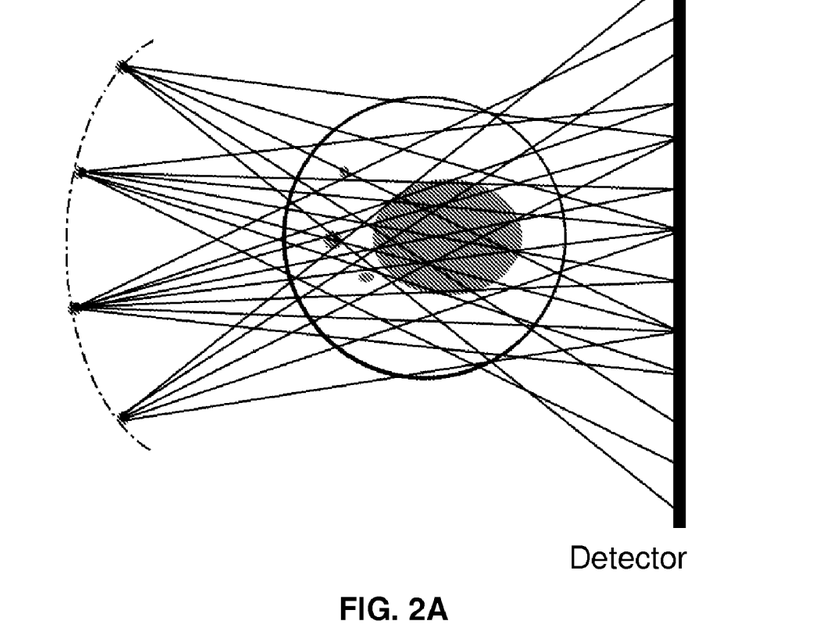
FIG. 2a is a coronal view of a stationary breast (large circle) being imaged with conventional digital tomosynthesis, showing the central region of the breast (shaded circle), x-rays (lines), and the position of the x-ray tube (large dark dots) relative to the detector at different points in time over a small angular arc.
Figure 2B:
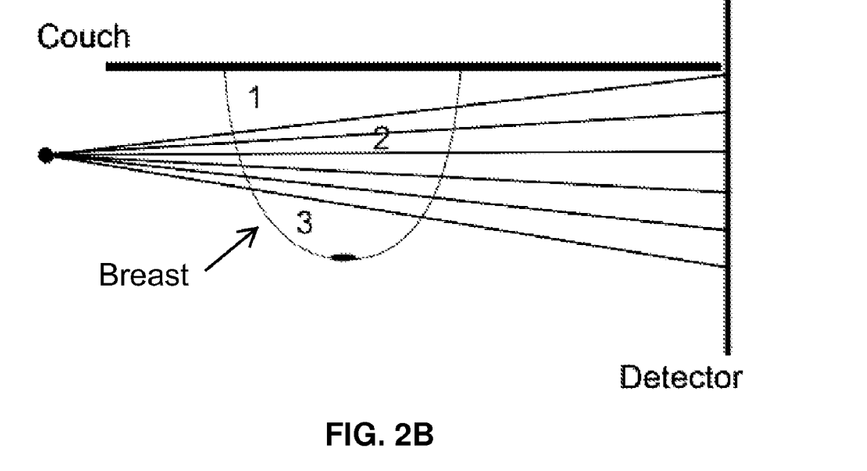
FIG. 2b is a vertical cross-sectional view of a stationary breast being imaged with conventional digital tomosynthesis using the same imaging geometry of FIG. 2a and showing that, while region 2 is traversed by the x-rays (lines), regions 1 and 3 are not traversed (or are undersampled).

FIG. 2a, which is a coronal view of a stationary breast (large circle) being imaged with conventional digital tomosynthesis and showing the central region of the breast (shaded circle), x-rays (lines), and the position of the x-ray tube (large dark dots) relative to the detector at different points in time over a small angular arc, imaging of a stationary breast with digital tomosynthesis results in insufficient beam overlap in the peripheral region of the breast, i.e., the region proximal and distal to the source of the x-ray (e.g., x-ray tube). Only the central region of the breast receives the maximal overlap of x-rays, thereby enabling the use of various computer algorithms to construct a clear image of the central region of the breast only. As shown in FIG. 2b, which is a vertical cross-sectional view of a stationary breast being imaged with conventional digital tomosynthesis using the same imaging geometry of FIG. 2a but at a single point in time over a single arc, while region 2 is traversed by the x-rays, regions 1 and 3 are not traversed. Reconstruction of the images results in non-uniform resolution, with poor resolution in the Z direction (i.e., direction of chest wall to nipple) and less poor resolution in the plane of rotation.

Figure 1B:
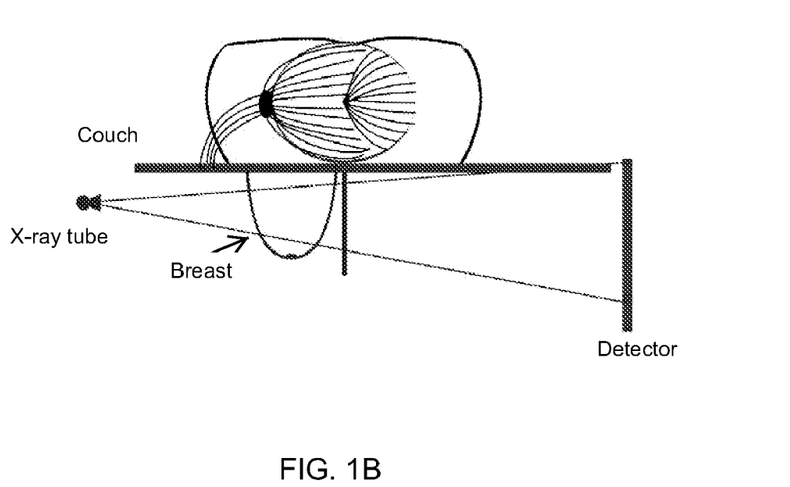
FIG. 1b is a head-on view of a patient lying prone on a couch with her right breast positioned in a channel (or right opening) of the couch relative to the x-ray tube and detector.
Figure 3:
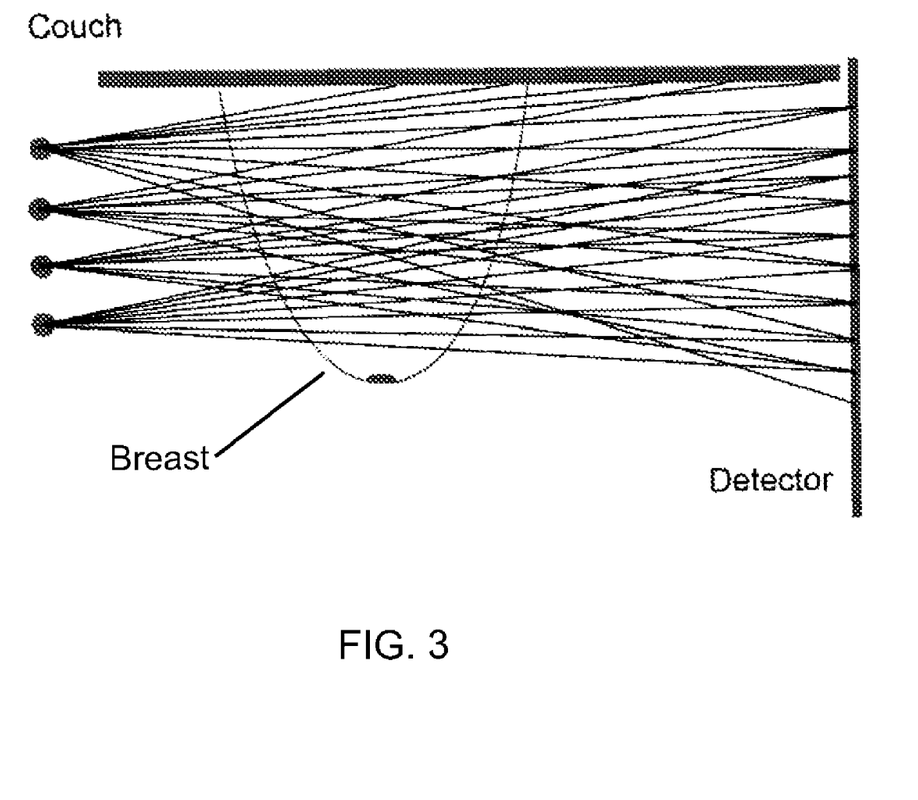
FIG. 3 is a vertical cross-sectional view of a breast being imaged with translational digital tomosynthesis in accordance with the present disclosure and showing that the zigzag scanning pattern allows the entire breast to be traversed by the x-rays (lines) emitted by the scanning x-ray tube (large dark dots) without missing or undersampling any region.
Figure 4A:
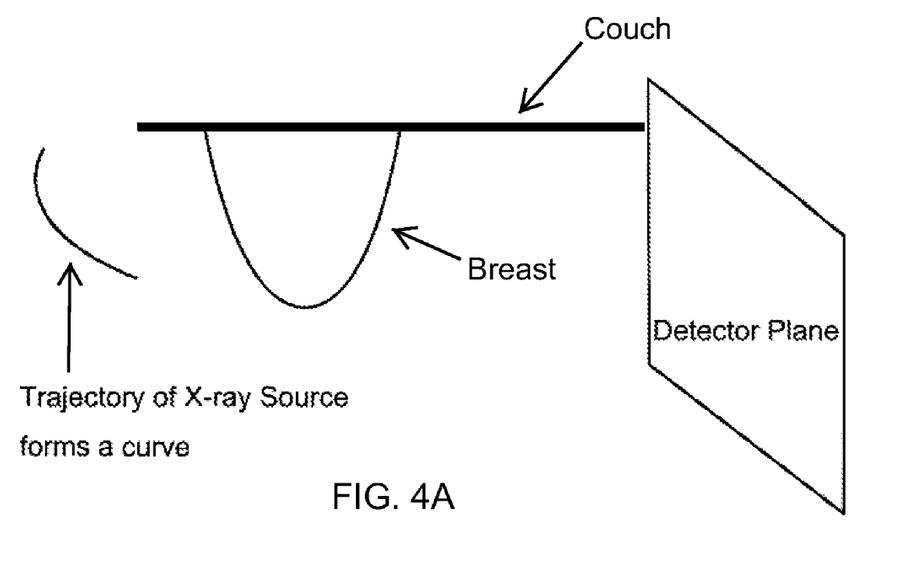
FIG. 4a is a schematic diagram of the breast in FIG. 1b showing that the trajectory of the x-ray source relative to the breast in accordance with conventional digital tomosynthesis is a curve.
Figure 4B:
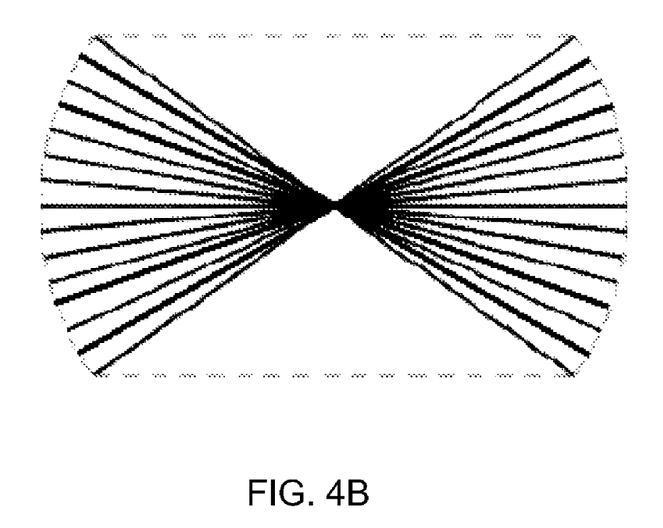
FIG. 4b shows the corresponding coverage in the frequency domain for the trajectory in FIG. 4a as a two-dimensional space covering two pie-shaped areas of a circular region.
Figure 5A:
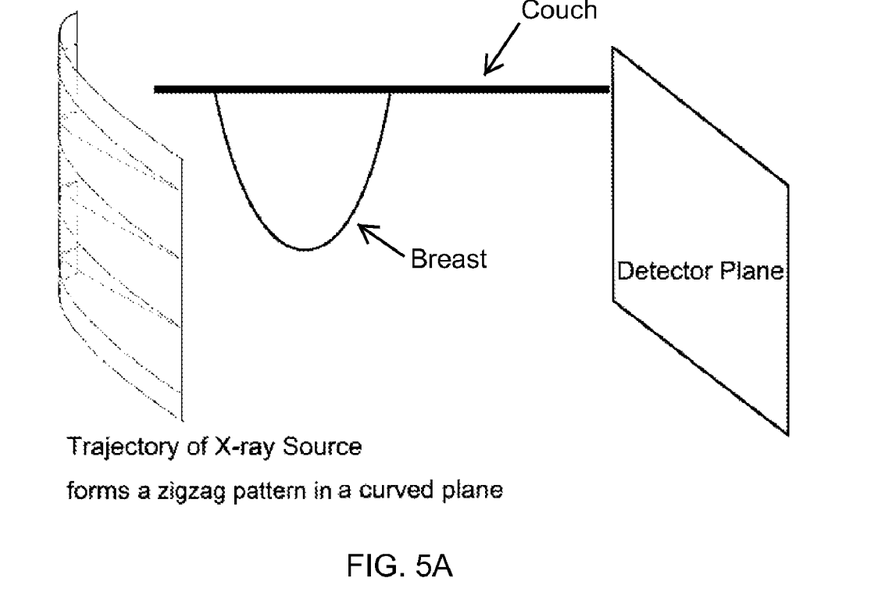
FIG. 5a is a schematic diagram of the breast in FIG. 1b showing that the trajectory of the x-ray source relative to the breast in accordance with the present disclosure is a zigzag pattern on a three-dimensional plane.
Figure 5B:
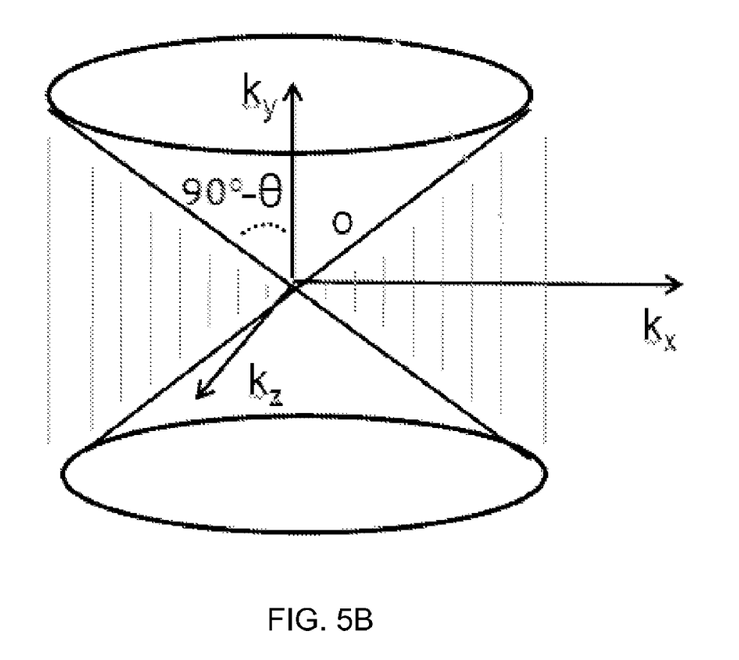
FIG. 5b shows the corresponding sampling space in the frequency domain for the trajectory in FIG. 5a as a three-dimensional space covering a cylinder minus the two opposing conical regions.

As shown in FIG. 3, which is a vertical cross-sectional view of a breast being imaged in accordance with the present disclosure (the breast is moved down and/or up in the x-ray field), movement of the breast in the field while scanning with x-rays increases the overlap between co-planar and non-co-planar beams such that computer algorithms can compute the attenuation coefficients for all regions of the breast. As shown in FIG. 4a, which is a schematic diagram of the breast in FIG. 1b, the trajectory of the x-ray source relative to the breast in accordance with conventional digital tomosynthesis is a curve. FIG. 4b shows the corresponding sampling space in the frequency domain for the trajectory in FIG. 4a as a two-dimensional space covering two pie-shaped areas of a circular region. FIG. 5a is a schematic diagram of the breast in FIG. 1b showing the trajectory of the x-ray source relative to the breast in accordance with the translational DTM of the present disclosure. The trajectory is a zigzag pattern on a three-dimensional plane (i.e., as part of a cylinder). FIG. 5b shows the corresponding sampling space in the frequency domain for the trajectory in FIG. 5a as a three-dimensional space covering a cylinder subtracted by two opposing cones sharing a common vertex at the origin. This three-dimensional sampling space is larger and more evenly covers the entire frequency domain. With that said, it is important to point out that the angle of the source of the x-ray can be varied during scanning, such that the surface, which is perpendicular to the central ray of the cone beam, can result in a spherical or parabolic trajectory.

Figure 6:
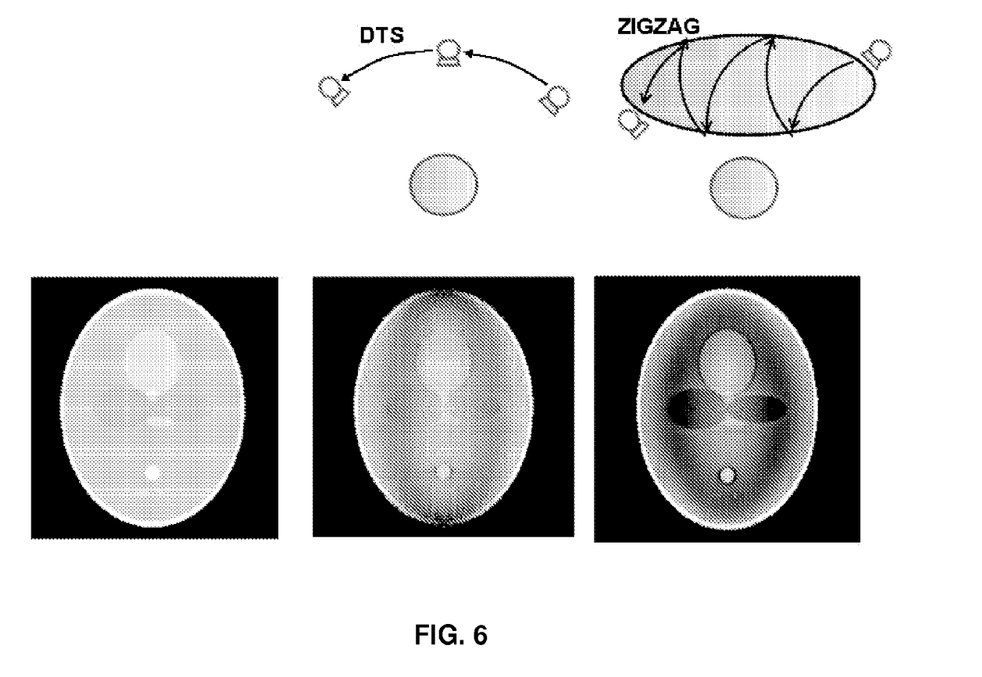
FIG. 6 shows a comparison of the quality of images achievable with conventional digital tomosynthesis (DTS) and with the translational digital tomosynthesis of the present disclosure. The left image shows a slice of a digitally created phantom (the truth), the middle image shows the same slice reconstructed by making projections by rotating the x-ray source along a single arc in accordance with conventional DTS, and the right image shows the same slice reconstructed by scanning the x-ray source back and forth while translating the phantom through the beams in accordance with the present disclosure.

FIG. 6 shows a comparison of the quality of images achievable with conventional DTM and with translational DTM of the present disclosure. The left image is a slice of a digitally generated phantom containing objects of different sizes and contrasts. The middle image shows the same slice re-constructed using projections from a single-arc scan according to conventional DTM. The right image shows the same slice re-constructed using projections from a zigzagged scan according to the translational DTM of the present disclosure. The right image better represents the slice (the left image), with more details, less noise, and fewer artifacts, than the middle image.

Figure 7:
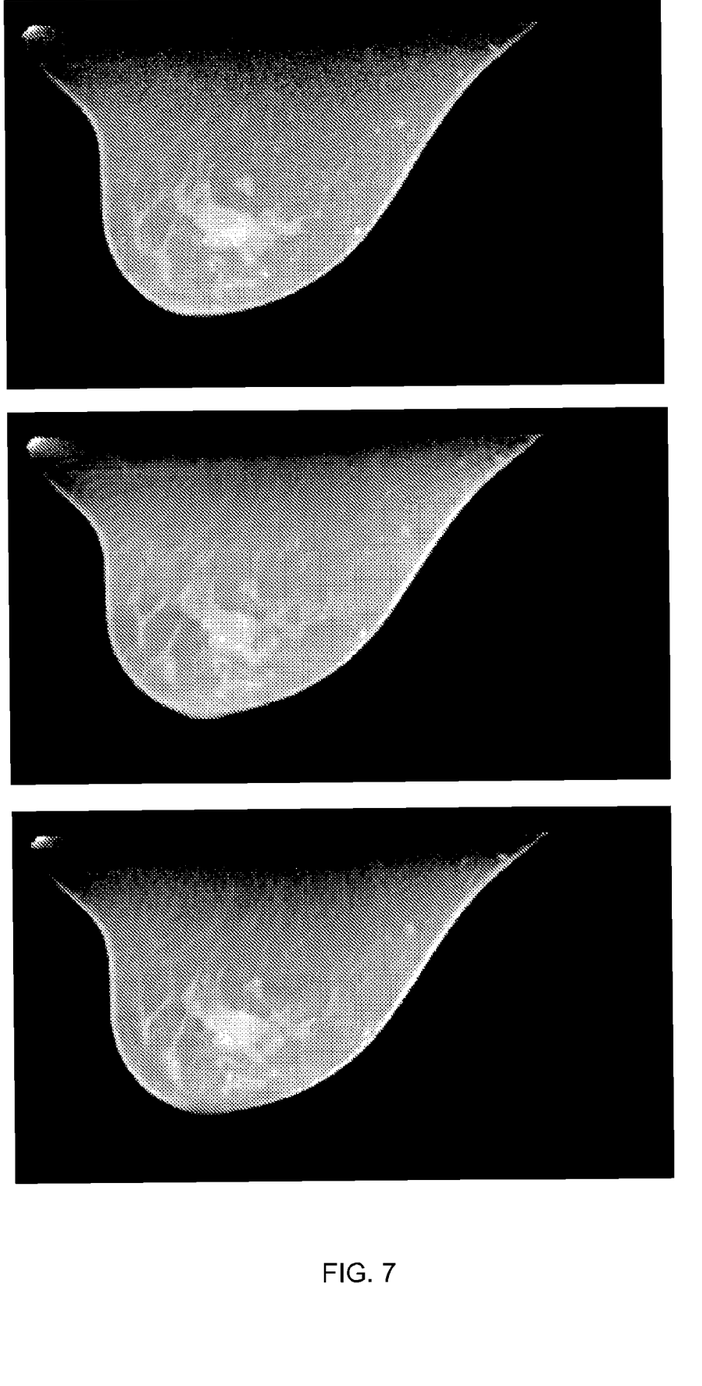
FIG. 7 shows a comparison of a slice of a female breast from a three-dimensional CT scan (top) with a computer-simulated conventional tomosynthesis scan (single 120° arc with 120 projections) of the same breast (middle) and a computer-simulated translational tomosynthesis scan of the same breast in accordance with the method of the present disclosure (bottom).

FIG. 7 shows a comparison of the quality of images of a female breast reconstructed from projections acquired in a full rotation (top), in a partial rotation of 120° as in a conventional DTM (middle), and from a zigzagged scan pattern according to the translational DTM of the present disclosure (bottom). The top image serves as the gold standard because it is the full CT geometry. The bottom image shows better clarity of the details and less peripheral artifacts than the middle image, illustrating the advantage of the translational DTM of the present disclosure.

The method can further comprise constructing a three-dimensional image of the breast in its natural shape alone or in further combination with analyzing the three-dimensional image of the breast, such as for diagnosis or therapy. The method enables the location of a tumor to be determined accurately for subsequent local treatment.

The couch comprises a channel or left and right openings for receiving the left or right breast, respectively, of the patient lying prone on the couch. The length of the couch should be sufficient to accommodate women as short as about 4'10" to as tall as about 6'6". The width of the couch should be sufficient to accommodate comfortably women weighing as little as 90 lbs. to as much as about 300 lbs. The width of the couch can vary somewhat along its length, e.g., being wider in the torso region and narrower in the leg region. The couch can be made from any radio-translucent material, such as one or more layers of hard plastic foam placed between two layers of carbon fibrous material. Optionally, the surface of the couch can comprise a top layer of a self-molding medium so as to provide a custom fit for the patient, thereby stabilizing the patient during imaging. For example, the couch can be covered with a vacuum bag filled with Styrofoam beads. The patient could lie on the vacuum bag, when the contents are not under vacuum, and adopt a comfortable position. A vacuum then could be applied to the contents to maintain the contours generated in the beads by the patient's body. Also optionally, the couch comprises one or two breast shields, which is/are removeably attached to the couch or slidably mounted to the channel and which keep(s) the breast, which is not being imaged, from entering the field and preferably shields that breast from radiation. If one or two breast shields are slidably mounted to the channel of the couch, the couch preferably further comprises a means of engaging the edge of the shield(s) so that it/they can be slid from one position to another. The couch is supported by a base support, which can be placed on a floor, in the presence or absence of a platform, or mounted on a wall.

The position of the couch can be driven by one, two or three motors, e.g., analog or digital motors, so that movement in at least one axis, such as the vertical axis, up to three axes of motion can be achieved. Movement in at least the vertical axis (i.e., the axis perpendicular to the top of the couch) is preferred. Redundant positional sensors can be used to ensure positional accuracy. The motor(s) can be housed in the base support of the couch. The movement of the couch is preferably controlled by a computerized control system. Preferably, the couch is configured to at least minimize, if not eliminate, back strain. For example, the portion of the couch supporting the lower body can be lowered, thereby reducing strain on the lower back. Preferably, the couch is also configured to allow the arms to rest on either side of the head, preferably with elbows bent, so as to maximize exposure of the outer quadrants of the breast. The lower portion of the couch also can be designed to allow the contralateral leg to be at a retracted position to reduce the pressure of the contralateral breast and improve patient comfort.

The x-ray source and the detector are placed on opposite sides of the couch, at or below the bottom surface of the couch. It will be understood by those ordinarily skilled in the art that more than one x-ray source, such as an array, and more than one detector can be used. The x-ray source can be any suitable source, such as a conventional x-ray tube, which is moved to achieve scanning, or a cold cathode carbon nanotube x-ray tube, which can be used as part of an array and, due to their small size, can be arranged along an arc. If an array is used, the x-ray sources in the array don't have to be moved to achieve scanning; rather, they can be fired in accordance with a programmed sequence, e.g., consecutively, preferably in a multiplexed fashion. Consecutive firing of the tubes allows the breast to be moved up and down continuously in the field for faster imaging. If the x-ray source is to be moved to achieve scanning, preferably the x-ray source can be moved in at least one direction, such as vertically (i.e., perpendicular to the floor and couch), so that it can scan the breast while all or a portion of it is in the field between the x-ray source and the detector. Also preferably, the x-ray source generates a cone beam. Any suitable detector also can be used. For example, the detector can be a two-dimensional array of x-ray detectors or a flat-panel detector array, such as amorphous silicon detectors commonly used for x-ray imaging. Examples of such set-ups are depicted in FIGS. 1 and 2. If the x-ray source is moving during scanning of the breast, the detector should move in synchrony with the x-ray source such that images of the breast are projected onto the detector. The movement or firing of the x-ray source and the movement of the detector can be controlled by a computerized control system, which can be the same computerized control system controlling the movement of the couch or a separate computerized control system.

The images of the breast, which are projected onto the detector (i.e., projection images), are read at a high frame rate, preferably greater than about 10 frames/second, by a computer and stored in a memory for subsequent three-dimensional image reconstruction of the breast. The read-outs from the detector preferably are multiplexed. Alternatively, the contributions from the different x-ray projections can be separated, so that the projections can be used independently. Construction of a three-dimensional image of the breast using digital tomosynthesis requires all of the voxels in the breast to be traversed by radiation beams from different directions or covered in a large number of projections. The greater the number of independent projections, the easier it is to apply a computer algorithm and determine the attenuation of the beam by each of the voxels.

The contrast and resolution of the constructed three-dimensional image of the breast in its natural shape can be improved, thereby enhancing the conspicuity of any tumor that might be present, by using a subtraction method, such as dual energy digital subtraction. For example, while the breast is moved in one direction, such as down, into/within the field between the source of radiation and the detector due to movement of the couch in a downward direction, the breast is exposed to x-rays of a given energy potential. Then, while the breast is moved in the other direction, such as up, out of/within the field between the source of radiation and the detector due to movement of the couch in an upward direction, the breast is exposed to x-rays of a different energy potential. The two-dimensional images then can be digitally subtracted before applying an image reconstruction algorithm. For example, the highest contrast (i.e., attenuation difference) between cancerous tissue (i.e., dense tissue and calcification(s)) and normal tissue (i.e., mostly adipose tissue) is achieved at an energy between about 20 kV and about 60 kV. However, an x-ray tube only creates a spectrum of energies from a few kV to the highest potential. Besides hardening (i.e., adding filters to attenuate preferentially x-rays of lower energy), there are limited means of altering the energy spectrum. Over-filtering attenuates the entire spectrum, adding scatter and causing image blurring. Dual energy digital subtraction enables the optimal energy band to be selected so as to maximize contrast between a particular tissue of interest (i.e., cancerous tissue) and surrounding tissue (e.g., muscle, adipose, and blood vessels). When contrast agents of high atomic number Z, such as Iodine, are used, the tumor, which is normally more vascular, takes up the contrast more readily. At energies below 100 kV, photo-electric interaction, with the likelihood proportional to the $Z^3$, will be more dominant in the tumor. While at energies greater than 100 kV, photo-electric interaction diminishes and Compton interaction dominates. Subtractions of the images acquired at these two energies will greatly enhance the regions of larger uptake of the contrast agent. The prone imaging geometry also makes the imaging less susceptible to breathing-induced motion. This fact also allows performance of temporal subtraction with two scans using the same lower, photo-electric dominant, energy but separated by a sufficient period of time (e.g., minutes) to allow the contrast agent to wash-off.

Thus, the method can, and preferably does, further comprise constructing a three-dimensional image of the breast in its natural shape based on the cross-sectional images obtained. A three-dimensional image can be constructed using tomosynthesis reconstruction algorithms as known in the art (see, e.g., Rakowski et al., Med. Phys. 33(8): 3018-3032 (2006)). Examples of such algorithms include, but are not limited to, filtered back projection methods (see, e.g., Stevens et al., Med. Phys. 28: 372-380 (2001), in re the use of slightly different filters), matrix inversion approaches (see, e.g., Webber, U.S. Pat. No. 5,668,844), and iterative techniques (also known as constrained iterative restoration; see, e.g., Suryanarayanan (2000), supra), and algebraic reconstruction techniques (ART). Such algorithms can be adopted and modified as necessary by those of ordinary skill in the In view of the above, also provided is a system for use in the method. The system comprises (i) a couch comprising a channel or right and left openings for placement of the right and left breasts, respectively, a base support, at least one motor, which is operably connected to the couch and which moves the couch in a vertical axis of motion, and a computerized control system, which controls the movement of the couch, (ii) an x-ray source, and (iii) a detector. The system optionally comprises a layer of a self-molding medium on the top surface of the couch, and/or one or two breast shields, which are removeably attached to the couch or slidably mounted to the channel.

Given that the breast is exposed to more radiation using this technique, this technique is more suitable for imaging guidance for radiation (or other) therapy or surgical removal of breast cancer than for breast cancer screening. With that said, the method and equipment described herein can be adapted for imaging of other parts of the body, such as the abdomen and the pelvis.

The following example serves to illustrate the present disclosure. The example is not intended to limit the scope of the present disclosure in any way.

EXAMPLE

This example describes a simulation of the method in accordance with the present disclosure.

The method of the present disclosure was simulated using an object represented by a conventional CT scan of a cancerous breast of a woman in the prone position. The scan was taken at 120 kV and a slice thickness of 1.5 mm. The expected detector signals were generated by ray-tracing through the data set using the scanning and translation employed in accordance with the method of the present disclosure. The results are shown in FIG. 8, in which FIG. 8a is a single slice of a three-dimensional CT scan of a breast and FIG. 8b is a simulated single slice of a translational digital tomosynthesis scan of the same location of the breast as in FIG. 8a. Even with a relatively high energy mono-energetic beam (50 kilo electron Volt (keV)) and poor resolution of the object data set, the method of the present disclosure improves contrast over conventional CT with 120 kV beam rotating around the patient.

A three-dimensional image of the breast can be constructed using a reconstruction algorithm employing an interactive correction. Attenuation coefficients can be estimated from the first scan. If the estimation is inconsistent with a subsequent scan, new estimates can be generated.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation (s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of imaging a breast of a human, which method comprises:
   (i) having a patient lie prone on a computer-controlled couch, which comprises a channel or left and right openings for placement and imaging of the breasts; and
   (ii) repeatedly imaging the breast using an x-ray source and a detector, which are on opposite sides of the couch, while moving the couch down and up, such that the breast moves down and up in the field between the x-ray source and the detector and images of the breast are projected onto the detector;
   wherein the x-ray source is either a movable x-ray source that scans back and forth along the side of the couch or an array of x-ray sources that fires in a programmed sequence back and forth along the side of the couch, and
   wherein the detector is movable and moves in synchrony with the movable x-ray source or the firing of the array of x-ray sources,
   whereupon the breast of a human is imaged.

2. The method of claim 1, wherein imaging the breast as it moves down in the field is conducted with x-ray of a given energy potential and imaging of the breast as it moves up in the field is conducted with x-ray of a different energy potential.

3. The method of claim 2, wherein the breast is in its natural shape and the method further comprises constructing a three-dimensional image of the breast from the projection images of the breast that were projected onto the detector while the breast was moving down in the field and a three-dimensional image of the breast from the images of the breast that were projected onto the detector while the breast was moving up in the field.

4. The method of claim 3, which further comprises enhancing the contrast and the resolution of the three-dimensional images.

5. The method of claim 4, wherein the contrast and the resolution of the three-dimensional images are enhanced using dual energy digital subtraction.

6. The method of claim 1, which further comprises constructing a three-dimensional image of the breast in its natural shape using a three-dimensional image reconstruction algorithm.

7. The method of claim 6, which further comprises analyzing the three-dimensional image of the breast.

8. The method of claim 1, wherein the computer controlled couch further comprises (i) a top layer of a self-molding medium, (ii) one or two breast shields, or (iii) a top layer of a self-molding medium and one or two breast shields, wherein the one or two breast shields of (ii) or (iii) is/are removably attached to the couch or slidably mounted to the channel and position the left or right breast of the patient in the channel or the left or right opening, respectively.

9. The method of claim 1, wherein the movement or the firing of the x-ray source(s) is in a zig-zag pattern in a curved plane relative to the breast being imaged.

10. A system for imaging of a human's breast, which system comprises (i) a couch comprising a channel or right and left openings for placement of the right and left breasts, respectively, a base support, at least one motor, which is operably connected to the couch and which moves the couch in a vertical axis of motion, and a computerized control system, which controls the movement of the couch, (ii) an x-ray source, and (iii) a detector, wherein:
   the x-ray source and the detector are on opposite sides of the couch,
   there is a field between the x-ray source and the detector through which the breast is moved when the at least one motor, which is operably connected to the couch, moves the couch in the vertical axis of motion,
   the x-ray source is either a movable x-ray source, which scans back and forth along the side of the couch while the breast is moved along a vertical axis in the field between the x-ray source and the detector, or an array of x-ray sources, which fires in a programmed sequence back and forth along the side of the couch while the breast is moved along a vertical axis in the field between the array of x-ray sources and the detector, and
   the detector is movable and moves in synchrony with the movable x-ray source or the firing of the array of x-ray sources.

11. The system of claim 10, wherein the system further comprises (i) a layer of a self-molding medium on the top surface of the couch, (ii) one or two breast shields, or (iii) a layer of a self-molding medium on the top surface of the couch and one or two breast shields, wherein the one or two breast shields of (ii) or (iii) is/are removably attached to the couch or slidably mounted to the channel.

12. The system of claim 10, wherein the at least one motor is a first motor and a second motor, wherein the first motor and the second motor are operably connected to the couch, the first motor moves the couch in a vertical axis of motion, and the second motor moves the couch in a second axis of motion.

13. The system of claim 10, wherein the at least one motor is a first motor, a second motor, and a third motor, wherein the first motor, the second motor and the third motor are operably connected to the couch, the first motor moves the couch in a vertical axis of motion, the second motor moves the couch in a second axis of motion, and the third motor moves the couch in a third axis of motion.

14. The system of claim 10, wherein the movement or the firing of the x-ray source(s) and the movement of the detector are controlled by the computerized control system that controls the movement of the couch or a separate computerized control system.

15. The system of claim 10, wherein the movement or the firing of the x-ray source(s) is in a zig-zag pattern in a curved plane relative to the breast being imaged.

* * * * *